United States Patent [19]

Helms et al.

[11] Patent Number: 4,619,251
[45] Date of Patent: Oct. 28, 1986

[54] PENILE PROSTHESIS HAVING AN ACTUATOR MEANS INTERACTING WITH A MEMBER AND ARTICULATED COLUMN

[75] Inventors: Richard A. Helms, Elk River, Minn.; Gerald W. Timm, San Juan Capistrano, Calif.; Donald L. Sandford, Lauderdale, Minn.

[73] Assignee: Dacomed Corporation, Minneapolis, Minn.

[21] Appl. No.: 775,782

[22] Filed: Sep. 13, 1985

Related U.S. Application Data

[63] Continuation-in-part of Ser. No. 604,022, Apr. 26, 1984, Pat. No. 4,541,420.

[51] Int. Cl.⁴ .................................................. A61F 5/00
[52] U.S. Cl. ......................................... 128/79; 623/12
[58] Field of Search ...................... 128/79; 623/11, 12; 52/108

[56] References Cited

U.S. PATENT DOCUMENTS

| | | | |
|---|---|---|---|
| 3,349,526 | 10/1967 | Schuster | 52/108 |
| 3,492,768 | 2/1970 | Schuster | 52/113 |
| 3,987,789 | 10/1976 | Timm et al. | 128/79 |
| 4,066,073 | 1/1978 | Finney et al. | 128/79 |
| 4,151,840 | 5/1979 | Barrington | 128/79 |
| 4,151,841 | 5/1979 | Barrington | 128/79 |
| 4,187,839 | 2/1980 | Nuwayser et al. | 128/79 |
| 4,392,562 | 7/1983 | Burton et al. | 128/79 |
| 4,522,198 | 1/1985 | Timm et al. | 128/79 |

Primary Examiner—Stephen C. Pellegrino
Attorney, Agent, or Firm—Merchant, Gould, Smith, Edell, Welter & Schmidt

[57] ABSTRACT

A bistable penile prosthesis (20) designed to be surgically implanted in the penis for the treatment of erectile impotence. The prosthesis includes an articulated column (26) enclosed within an outer elongated sheath (28). The articulated column (26) has segments (250) including interlocking means for reducing radial slippage between the facing ends of adjacent ones of the segments (250) whereby the likelihood of the segments (250) becoming disjointed is reduced.

13 Claims, 17 Drawing Figures

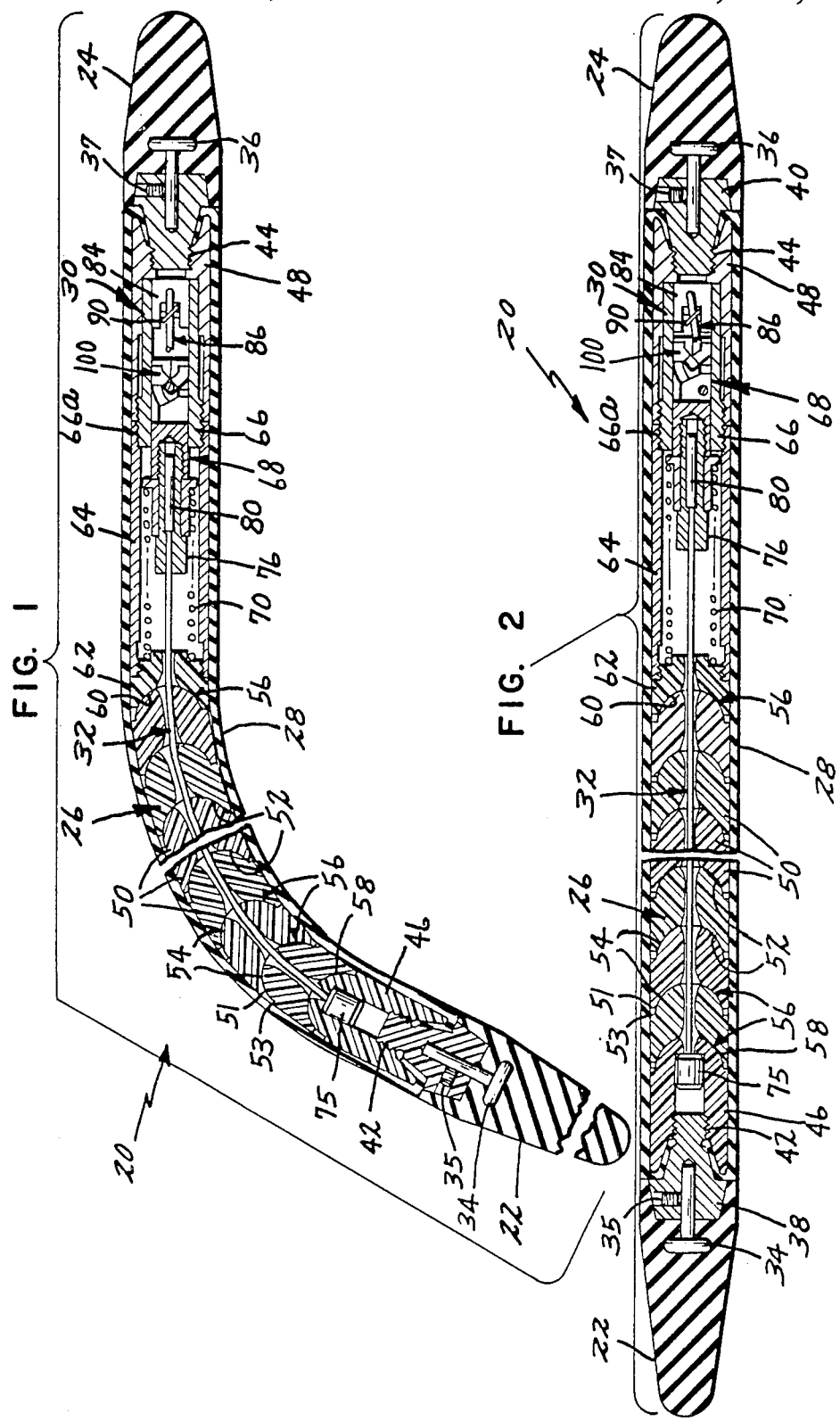

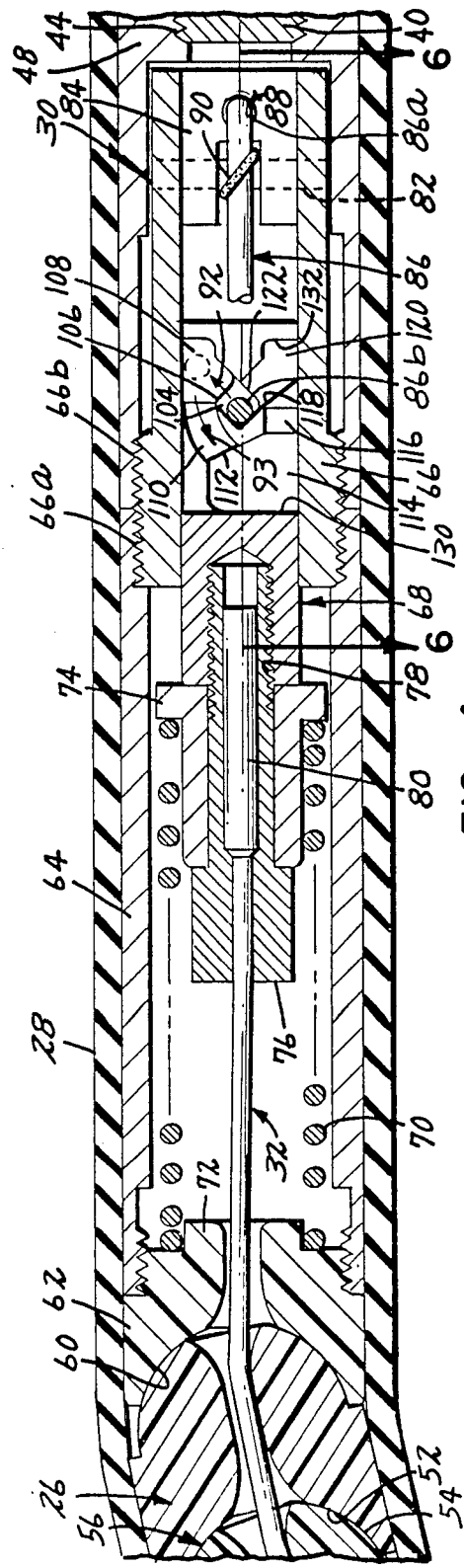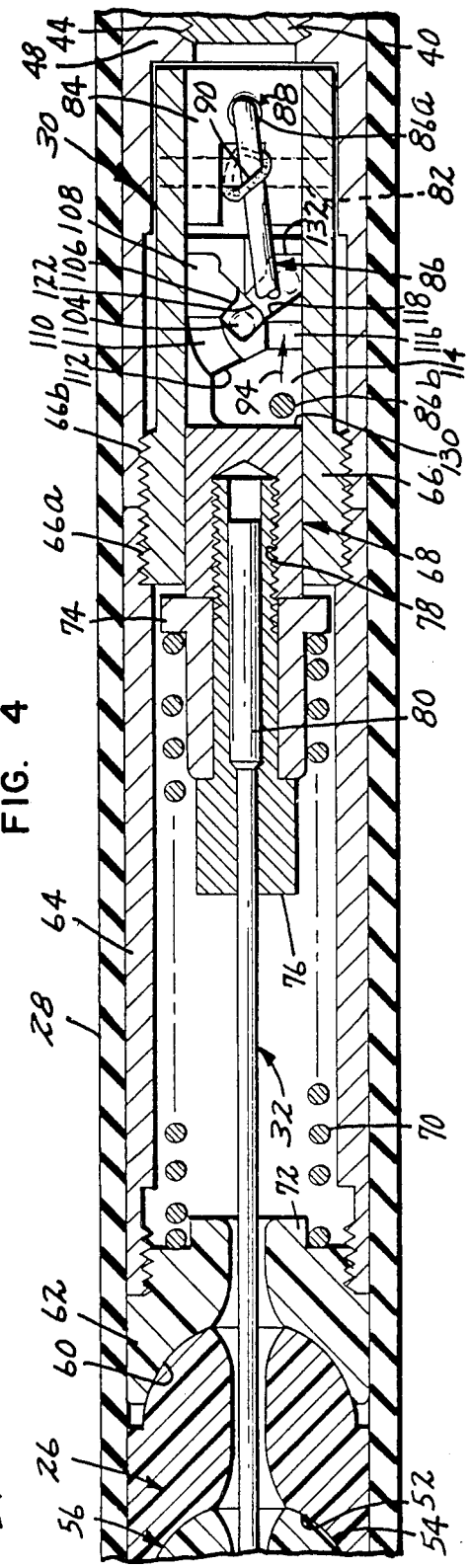

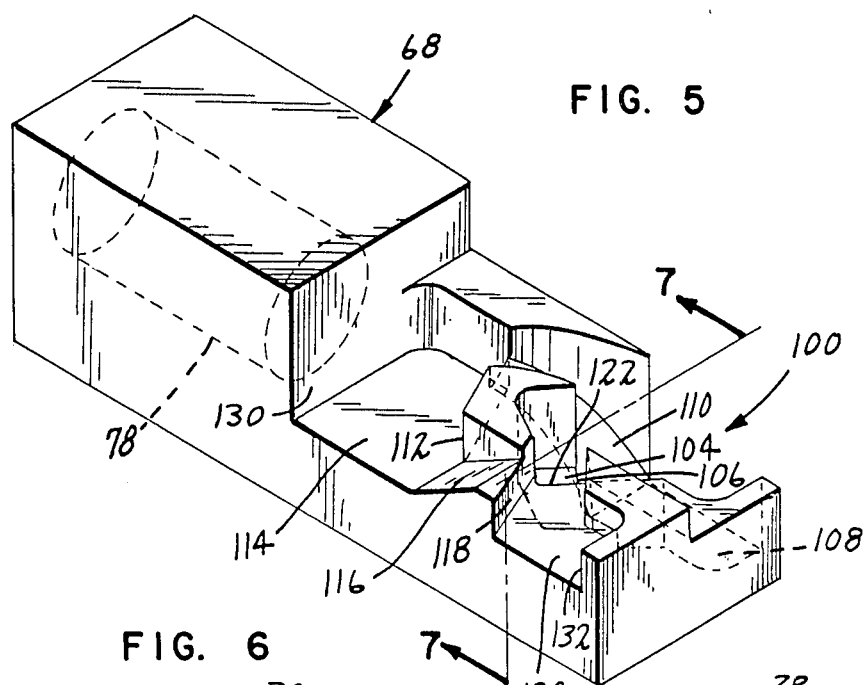
FIG. 5
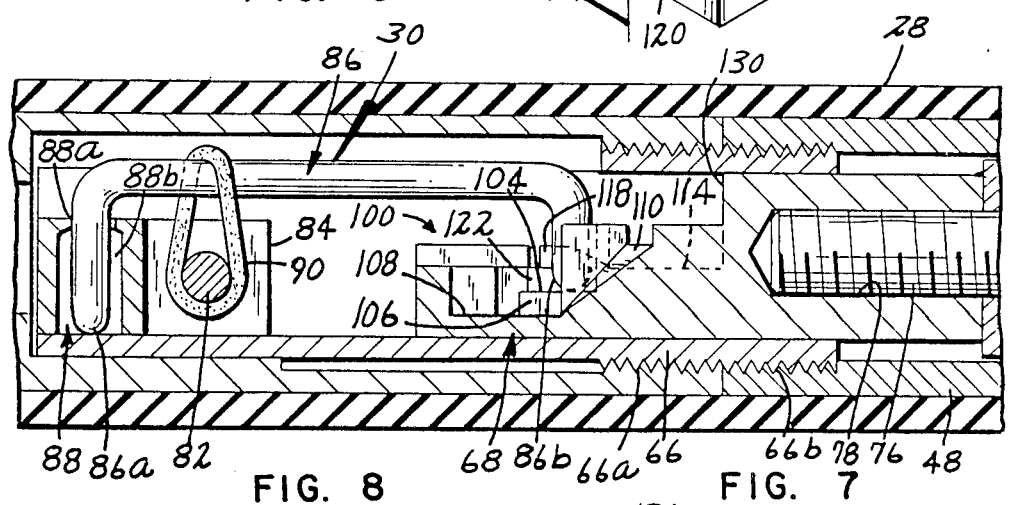
FIG. 6
FIG. 7
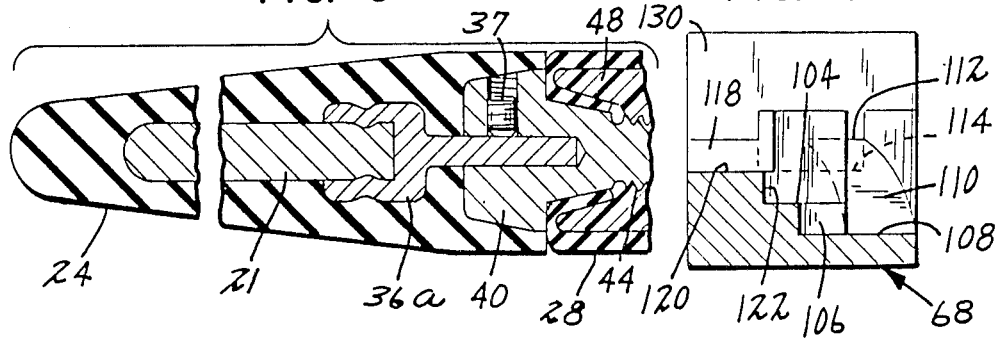
FIG. 8

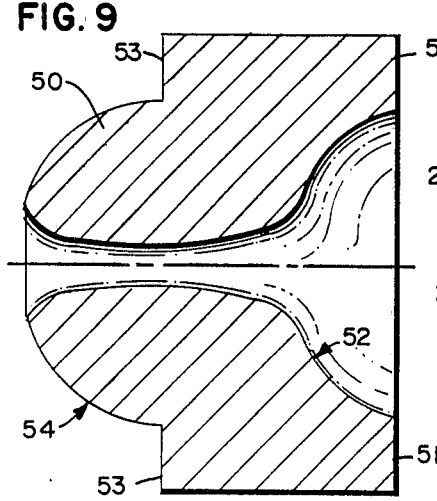
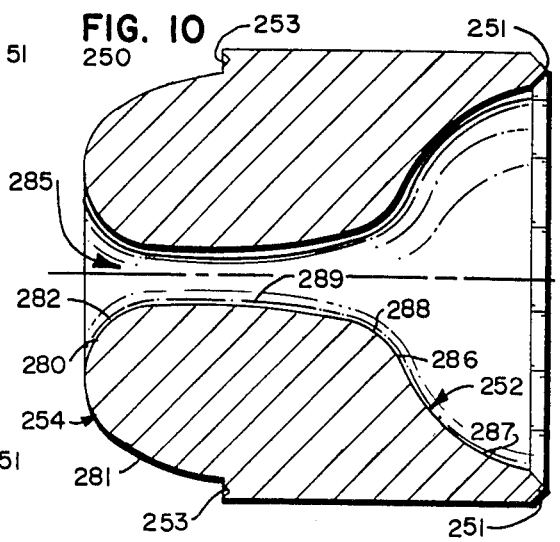
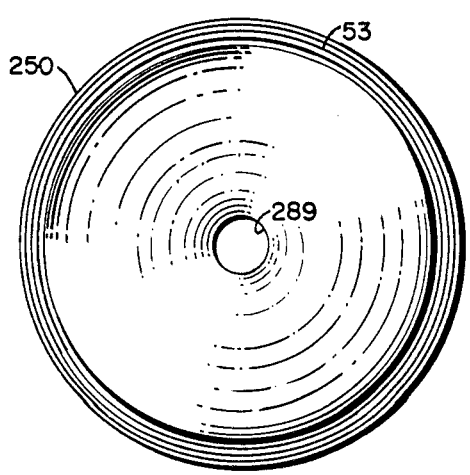
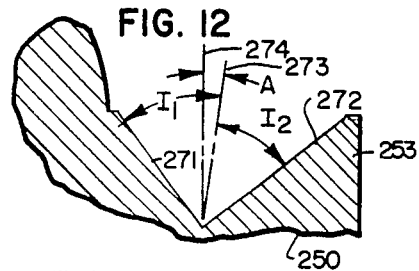
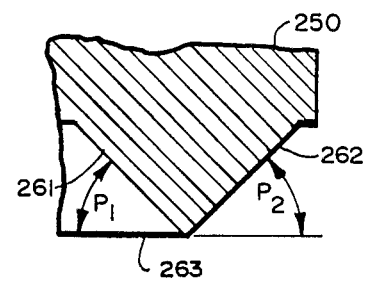
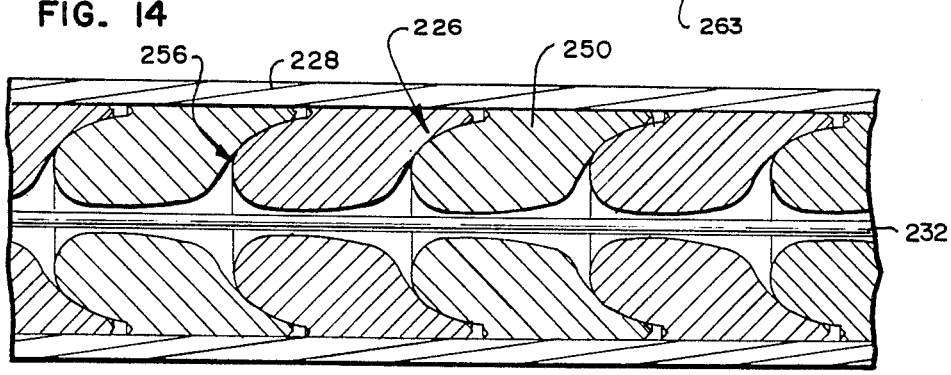

PENILE PROSTHESIS HAVING AN ACTUATOR MEANS INTERACTING WITH A MEMBER AND ARTICULATED COLUMN

This application is a continuation-in-part of application Ser. No. 604,022 filed Apr. 26, 1984 now U.S. Pat. No. 4,541,420.

BACKGROUND OF THE INVENTION

This invention relates to a penile prosthesis. More particularly, the present invention relates to a penile prosthesis including actuator means providing for volitional control of penile erection and return thereof to a flaccid condition.

The causes of male impotence are many and varied. Various approaches to treating impotence have been developed over the past two decades. Penile prostheses have been implanted within the penis to simulate an erectile state. For example, in Timm et al., U.S. Pat. No. 3,987,789, there is disclosed a prosthesis including an elongated malleable rod portion housed within a generally tubular physiologically inert plastic body. The malleable rod portion enables the prosthesis to be conformed to a variety of shapes by bending or twisting. During intercourse the prosthesis will maintain the penis in an erectile state and afterwards the penis may be positioned and maintained by the user in a convenient, comfortable position. The prosthesis depends upon its malleability to permit moving the penis to a convenient comfortable position. The flexibility and similar characteristics of the prosthesis are not controllable by the patient.

U.S. Pat. No. 3,954,102 to Buuck shows a penile erection system having two conditions. In one condition, the implanted prosthesis is controlled by varying the amount of fluid in cylinders within the prosthesis by squeezing an elastomeric bulb through the patient's skin to transfer fluid from a reservoir into cylinders in the prosthesis. Because the reservoir and bulb are positioned outside of the prosthesis within the patient's body, the implantation procedure is quite complex and the extensive tubing required to interconnect the various portions of the system increase the possibility of failure of the system.

Other implantable prosthesis have been developed which incorporate a reservoir pump and valving into the prosthesis itself as shown for example, in U.S. Pat. Nos. 4,369,771 and 4,353,360. Those systems still require pump and valving apparatus to be installed within the prosthesis and require the transfer of fluid from a reservoir into an inflatable portion for operation.

The present invention solves these and many other problems associated with currently available devices.

SUMMARY OF THE INVENTION

The present invention relates to a penile prosthesis having an elongated cylindrical body with a longitudinal axis and a distal end portion and a proximal end portion. The elongated cylindrical body being enclosed by an outer elongated sheath formed from a physiologically inert and pliable material. An articulated column of radiused segments is disposed intermediate of the distal end portion and the proximal end portion. The radiused segments have a concave surface portion proximate one end thereof and a convex surface portion proximate an opposite end thereof. The facing concave and convex surface portions of facings ones of the radiused segments cooperate to form ball and socket joint means between adjacent ones of the segments for enabling slidable movement therebetween. The radiused segments having proximate the facing ends thereof cooperating indentation and protuberance means for restricting radial movement between the facing ends of adjacent ones of the radiused segments. The indentation means being located proximate one end of the radiused segments and the protuberance means being located proximate the opposite end of the radiused segments. An elongated tension member extends longitudinally of the elongated cylindrical body. The tension member is fixed against longitudinal movement at a first end. The articulated column is axially journaled about the tension member. Switch means is enclosed within the sheath for switching the prosthesis between a rigid state and a flexible state, the switch means cooperating with the tension member and the articulated column for increasing the tension in the tension member and compressing the articulated column when switching the prosthesis to the rigid state.

The invention provides for a mechanical patient-controlled device for inducing penile erection upon manual activation. In particular, the invention is a surgically implantable mechanical penile prosthesis composed of an elongated cylindrical device which employs an articulated column characterized by a series of segments with slidable alternating ball and socket joints therebetween. The normal flexibility of the device permits the penis to normally remain in a flaccid state.

The prosthesis of the present invention is particularly advantageous in that it can be implanted surgically within the penis without regard to angular orientation thereby avoiding the possibility of failure if during implant or in use, the prosthesis partially rotates about its longitudinal axis. Accordingly, the prosthesis is designed to be generally symmetrical about its longitudinal axis.

Furthermore, the present invention provides for volitional control of erection, generating sufficient stiffness of the penis for intercourse, and permits user deactivation, whereby the penis recovers as a flaccid state.

Yet another advantageous feature of the present invention is that it readily enables patient activation and deactivation.

Furthermore, the present invention is designed to be implanted by conventional surgical procedures and is biologically compatible with the human body environment.

In addition, the present invention provides for activation/deactivation over many cycles of use.

Furthermore, the present invention enables the penis to obtain a flaccid state when the prosthesis is deactivated and provides sufficient rigidity for intercourse when the prosthesis is activated.

The present invention provides for greater rigidity when in the erect state and greater flaccidity and comfortable concealment when in the flacid state. In the flaccid state the prosthesis will hang downwardly due to the weight of the prosthesis and the penis so as to have a somewhat natural configuration.

Furthermore, the present invention is suitable for long term implants.

Additionally the present invention provides a prosthesis which can withstand higher loads while utilizing an actuator apparatus which functions in a small and confined space.

The present invention provides a prosthesis which includes a totally self-contained actuator apparatus for mechanically controlling the two phases of penile erection, the erect phase and the flaccid phase.

A preferred embodiment of the present invention is bistable. In other words it operates in either a flexible or a stiffened mode at the user's control. Activation and deactivation is achieved by manual bending of the penis, whereupon the prosthesis is alternately rigid or flaccid. Bending of the prothesis places a tension member in tension which causes a cam member of the actuator apparatus to be axially displaced, the actuator apparatus alternately securing the prosthesis in a deactivated, flaccid state or an activated, erect state.

In the preferred embodiment of the present invention, the articulated column is axially journaled about the longitudinally extending tension member. When the prosthesis is activated, the increased tension in the tension member and the compression of the articulated column induces a stress state in the prosthesis that displays bending stiffness. This is attributable to: (1) interfacial friction between the spheres and sockets in the column and (2) tension in the tension member.

Also in the preferred embodiment of the present invention, the actuator apparatus includes a cam member having a generally heart shaped ramp configuration and a cam follower member adapted for following said ramp configuration in only one direction. The cam member is slidably mounted for axial movement of the prosthesis and is interconnected to the tension member and is further biased away from the articulated column by a biasing member. Alternate bending of the prosthesis places the tension member in tension and causes the cam member to be displaced axially whereupon the cam follower follows the ramp configuration of the cam member. Upon ceasing the bending process, the cam member returns to a first longitudinal position or a second longitudinal position such that the prosthesis is in a flaccid state or an erect state.

Yet another feature of the preferred embodiment is that the articulated column includes a plurality of bend limiting segments forming cooperating ball and socket joints therebetween. The bend limiting segments have cooperating shoulder portions which limit the amount of pivotal movement of adjacent bend limiting segments.

Yet another feature of the preferred embodiment is the provision for varying sizes of distal and proximal end portions which are removably interconnected to the prosthesis to modify the overall length of the prosthesis to accomodate normal variations in the patient's intracorporal cavernosal length.

Still another feature of the preferred embodiment is the inclusion of a stiffening member providing additional rigidity to the distal end portion.

Yet another embodiment of the present invention includes an articulated column whose individual segments include indentation and protuberance means respectively positioned proximate opposite ends of each of the segments. Facing indentation and protuberance means of adjacent ones of the segments cooperate to prevent relative radial slippage or movement between adjacent ones of the segments when the prosthesis is bent. Moreover, the cooperating indentation and protuberance means provide a predefined pivot point between adjacent ones of the segments. Accordingly, this embodiment provides for a uniform radius of curvature.

In yet another embodiment of the present invention, the segments are provided with convex and concave surfaces at respective opposite ends of the segments. In one embodiment, the convex surface and concave surface each include a plurality of curves of uniform but different radiuses of cruvature which are tangentially interconnected so as to reduce or eliminate any sharp edges.

Still another embodiment of the present invention includes resilient biasing means interconnected to the tension member proximate one end of the tension member for exerting a predetermined axially directed force on the tension member such that if an opposing force is exerted on the tension member which is greater, the end of the tension member will be displaced, thereby reducing tension and preventing damage to the tension member which might otherwise be caused by excessive bending or distortion of the prosthesis.

These and various other advantages and features of novelty which characterize the invention are pointed out with particularity in the claims annexed hereto and forming a part hereof. However, for a better understanding of the invention, its advantages and objects attained by its use, reference should be had to the drawings which form a further part hereof, and to the accompanying descriptive matter, in which there is illustrated and described a preferred embodiment of the invention.

BRIEF DESCRIPTION OF THE DRAWINGS

In the drawings, in which like reference numerals and letters indicate corresponding parts throughout the several views:

FIG. 1 is a longitudinal axial sectional view of a preferred embodiment of the present invention in a deactivated or flaccid state;

FIG. 2 is a longitudinal axial sectional view of the embodiment shown in FIG. 1 in an activated or erect state;

FIG. 3 is an enlarged axial sectional view with portions broken away of the actuator apparatus of the embodiment shown in FIG. 1 in the deactivated or flaccid state;

FIG. 4 is an enlarged axial sectional view with portions broken away of the actuator apparatus of the embodiment shown in FIG. 2 in the activated or erect state;

FIG. 5 is an enlarged elevational view of the cam member of the actuator apparatus shown in FIGS. 1 and 2;

FIG. 6 is a sectional view as generally seen along line 6—6 of FIG. 3;

FIG. 7 is a sectional view as generally seen along line 7—7 in FIG. 5;

FIG. 8 is an enlarged sectional view of an alternate embodiment of the distal end portion;

FIG. 9 is an enlarged sectional view of a radiused segment of the articulated column shown in FIG. 1;

FIG. 10 is an enlarged sectional view of an alternate embodiment of a radiused segment;

FIG. 11 is a plan view looking at the convex surface of the embodiment shown in FIG. 10;

FIG. 12 is an enlarged fragmentary view of an indentation in accordance with the principles of the present invention.

FIG. 13 is an enlarged fragmentary view of an embodiment of a protuberance in accordance with the principles of the present invention; and FIG. 14 is a partial enlarged sectional view of an embodiment of an articulated column in accordance with the principles of the present invention utilizing the embodiment of the radiused segment shown in FIG. 10;

DETAILED DESCRIPTION OF A PREFERRED EMBODIMENT

Figure 15:
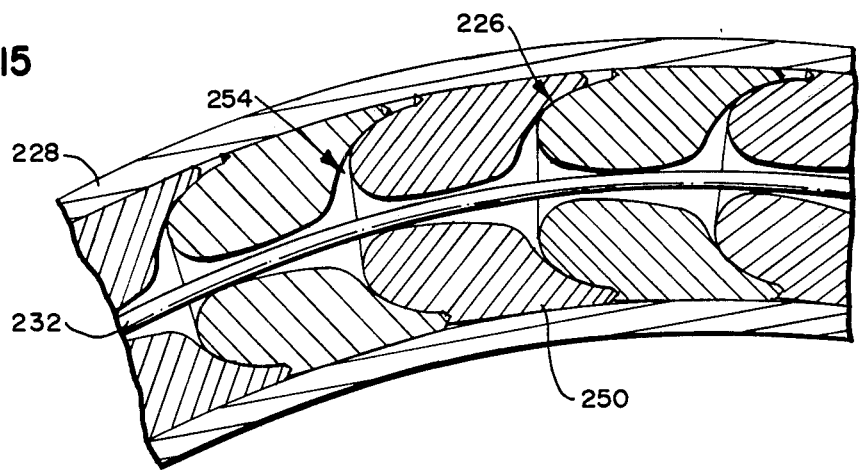
FIG. 15 is a view similar to that of FIG. 14, illustrating the articulated column being bent.

Referring now to the drawings, a preferred embodiment of a mechanical penile prosthesis in accordance with the principles of the present invenion is illustrated in FIGS. 1 and 2, the penile prothesis generally being referred to by the reference numeral 20. The prosthesis 20 is generally shown as an elongated member including a proximal end portion 22 and a distal end portion 24. An elongated articulated column 26 is positioned between the proximal and distal end portions 22 and 24 enabling pivotal or bending motion of the prosthesis 20 in all directions (360 degrees) about the longitudinal axis of the prosthesis 20. Interposed between the distal end of the articulated column 26 and the distal end portion 24 is an actuator apparatus 30. It will be appreciated that in other embodiments, the actuator apparatus 30 might be located between the proximal end portion 22 and the articulated column 26. The articulated column 26 is axially journaled about an axially extending elongated tension member 32 which extends from proximate the proximal end of the articulated column 26 to proximate the proximal end 22 of the actuator apparatus 30. The articulated column 26 and the actuator apparatus 30 are enclosed by a sheath 28 of physiologically inert and pliable material, preferably silicone rubber coated polytetrafluoroethylene which shields the prosthesis 20 from body tissue so as to prevent the growth of body tissue into the inner working elements of the prosthesis which would otherwise affect operation of the working elements of the prosthesis and interfere with its proper function. In addition, such growth of body tissue into the prosthesis might also result in damage to the body tissue. Accordingly, the sheath 28 also prevents tissue damage.

The actuator apparatus 30 in cooperation with the tension member 32 and the articulated column 26 provides the preferred embodiment of the present invention with bistable characteristics, i.e. the prosthesis 20 may be manually activated to a rigid/erect state as generally illustrated in FIG. 2 or deactivated to a flexible/flaccid state as generally indicated in FIG. 1. The prosthesis 20 remains in either of these two states until manually activated or deactivated.

The prosthesis 20 of the present invention is designed for implantation in the intracorporal cavernosal of the penis by conventional surgical procedures for treatment of erectile impotence. The prosthesis 20 is configured to generally match penile intracorporal cavernosal size so as to extend sufficiently proximally and distally when anchored within the penis and body cavity so as to induce an erected penile state generating sufficient stiffness of the penis for intercourse when activated and to provide the penis with flaccid characteristics when deactivated.

Accordingly, the present invention provides for volitional control of penile erection and return thereof to a flaccid state. Furthermore, the configuration of the present invention enables surgical implantation without regard for angular orientation and prevents malfunction if angular rotation is realized during use. In addition, the present invention is biologically compatible with the human body environment and enables activation/deactivation over many repetitive cycles of use.

More particularly, the proximal end portion 22 is tapered to assist in anchoring the prosthesis 20 in the body and the distal end portion 24 is bullet-or cone-shaped to adapt to the distal end of the penis. The proximal end portion 22 and the distal end portion 24 are provided in various lengths to accommodate normal variations in the patient's intracorporal cavernosal length, perferably ranging from one to eight centimeters. The appropriate length for each is selected at the time of implant as determined by the incision site and by the patient's total intracorporal cavernosal length. Preferably, the proximal end portion 22 and the distal end portion 24 are made from a semi-rigid material such as silicone rubber.

The proximal end portion 22 and the distal end portion 24 are attached to the segmented, flexible body of the prosthesis 20. This might be accomplished in any of several ways such as by a positive locking, snap-on mechaniam (not shown) or by threaded attachment of the end portions 22, 24 to the flexible body of the prosthesis 20. In the preferred embodiment, as generally illustrated in FIGS. 1 and 2, elongated T-shaped stainless steel pin members 34, 36 are securedly molded or embedded in the proximal end portion 22 and the distal end portion 24, respectively. The T-shaped pin members 34, 36 are slideably inserted into cylindrical apertures located in clamp members 38, 40 respectively. The T-shaped pin members 34, 36 are retained in the apertures of the clamp members 38, 40 by Titanium set screws 35 and 37. It will be appreciated that in the embodiment shown, the end portions 22, 24 may be readily replaced during the implantation process, if necessary, by simply folding back the silicone rubber material enclosing the set screws 35, 37 so that a hex-wrench can be utilized to loosen the set screws 35, 37. The clamp members 38, 40 in turn are threadedly attached at 42, 44, respectively to the flexible body of the prosthesis. The clamp members 38, 40 cooperate with wedge shaped members 46, 48, which are configured to receive the clamp members 38, 40 such that the end portions of the sheath 28 are wedged between the clamp members 38, 40, and the inside sloping walls of the members 46, 48. Accordingly, the sheath 28 is retained in position at the proximal and the distal end portions of the prosthesis 20.

As illustrated in FIG. 8, in an alternate embodiment of the distal end portion 24, particularly in the longer versions, a polymeric reinforcing rod 21 might be molded therein to provide extra stiffness. The reinforcing rod 21 is wedged and crimped into a modified pin member 36a designed for the longer distal end portion 24. The reinforcing rod 21 provides sufficient rigidity to prevent buckling but provides sufficient resiliency to provide for some bending action such that the reinforcing rod 21 can be concealed within the silicone rubber of the end portion 24 and yet not break or erode through the surfaces thereof after extended use thereof.

The articulated column 26 comprises a plurality of radiused segments 50. Each of the segments 50 has a concave surface 52 and a convex surface 54, the segments 50 being oriented such that the adjacent surfaces of the segments 50 cooperate to form ball and socket joints 56. The articulated column 26 is journaled axially to receive the tension member 32. The segments 50 as well as the other internal parts of the prosthesis are made from a surgically implantable material, preferably an implantable plastic, such as polyurethane, polysulfone, or polypropolene.

It will be appreciated that in alternate embodiments of the present invention, other elements with slidable cooperating surfaces may be utilized to form an articulated column.

In the preferred embodiment as illustrated in FIGS. 1 through 4, the segments 50 include a shoulder portion 51 about the periphery of the concave surface 52 and a corresponding shoulder portion 53 about the periphery of the convex surface 54, the shoulder portions 51, 53 of adjacent segments 50 cooperate to limit the amount of bending or pivotal movement which can occur at the junction of any two adjacent segments 50.

In the embodiment illustrated, the member 46 to which the sheath 28 is clamped, has a generally convex surface 58 adjacent the proximal end of the articulated column 26 to form a ball and socket joint with the articulated column 26.

Furthermore, a segment 62 at the distal end of the articulated column 26 and interconnected to the member 48 has a concave surface 60 thereby forming a ball and socket joint with the articulated column 26.

As shown in FIGS. 1 and 2, disposed intermediate of the distal end portion 24 and the distal end portion of the articulated column 26 is the actuator apparatus 30. It will be appreciated, that the actuator apparatus 30 might also be disposed intermediate of the proximal end portion 22 and the articulated column 26; however, for purposes of this specification the actuator apparatus 30 will be presumed to be positioned proximate the distal end portion 24.

The radiused segment 62 is threadedly interconnected at a distal end to a hollow housing 64 which is coaxially positioned within the sheath 28. The hollow housing 64 is in turn threadedly interconnected at an opposite end to a threaded portion 66a of a guide member 66 which is coaxially positioned within the sheath 28 and serves as a longitudinal guide for a cam member 68 illustrated in more detail in FIG. 5. As illustrated in FIG. 5, the cam member 68 has a generally rectangular base configuration. Accordingly, the guide member 66 defines a rectangular U-shaped channel which is open on a side facing the top of the cam member 68. The guide member 66 is in turn fixed against longitudinal movement by being threadedly attached to the segment 48 along a threaded portion 66b.

As illustrated in FIGS. 3 and 4, the housing 64 serves as a spring casing for a coil spring 70 which is mounted between a spring seat 72 on the segment 62 and a spring seat 74 adjacent the proximal end of the cam member 68. The coil spring is coaxially positioned about the tension member 32 which is fixedly secured at its proximal end by an anchor member 75 pivotally mounted in the member 46 and fixedly secured at its distal end by an anchor member 76 threadedly attached to a threaded aperture 78 in the cam member 68. The anchor member 76 cooperates with a member 80 crimped onto the end of the tension member 32 to securedly anchor the tension member 32 to the cam member 68.

As illustrated in FIG. 3 and 4, fixed against longitudinal movement by a cross pin 82 interconnected to the guide member 66 is a stationary mounting block 84 which pivotally supports a cam follower member 86 at a first end 86a in an aperture 88 for pivotal motion about an axis transverse with respect to the longitudinal axis of the prosthesis 20. As illustrated in FIG. 6, the aperture 88 has a narrowed portion 88a roughly the diameter of the end 86a and an enlarged portion 88b. The aperture 88 extends completely through the mounting block 84. The cam follower member 86 is retained in the aperture 88 by an O-ring 90, which might be made of silicone rubber, positioned around the cross pin 82 and the cam follower member 86 intermediate of the first end 86a and a second end 86b of the cam follower member 86.

As further illustrated in FIGS. 5 through 7, the cam member 68 has a generally heart shaped ramp configuration 100 with a plurality of horizontal surfaces, ramps, and vertically extending barriers providing for only one way travel therealong as generally indicated by the arrows 92, 93, and 94 in FIGS. 3 and 4 by the end 86b of the cam follower member 86 as the cam member 68 moves longitudinally of the prosthesis 20. The O-ring 90 also serves to bias the cam follower member 86 downwardly onto the ramp configuration 100 and the guide member 66 facilitates in retention of the cam follower end 86b on the ramp configuration 100.

In operation, the prosthesis 20 is activated by manually bending the prosthesis 20 downwardly into a curved shape. The bending action causes a displacement of the tension member 32, which because of its fixed length, results in increased tension in the tension member 32. When the force in the tension member 32 exceeds that of the coil spring 70, the cam member 68 moves longitudinally toward the articulated column 26. The geometry of the ramp configuration 100 is such that movement of the cam member 68 causes the cam follower 86 to move through the one way pattern on the ramp configuration 100. This movement causes the cam follower 86 to alternately lock the prosthesis 20 in the flaccid/flexible state as illustrated in FIGS. 1 and 3 and the erect/rigid state as illustrated in FIGS. 2 and 4 upon cessation of the bending movements. In the flaccid position, the tension in the tension member 32 is slight as is the frictional forces between the radiused segments 50 whereby the prosthesis is relatively flexible. In the erect/rigid state the cam member 68 is displaced longitudinally farther from the anchored end of the tension member 32 such that the tension member 32 is placed in tension and the frictional forces between the radiused segments 50 is increased whereby the prosthesis is relatively rigid.

More particularly, as illustrated in FIGS. 5 through 7, the ramp configuration 100 of the cam member 68 includes two inclined ramps 110 and 116 and four horizontal surface areas 104, 108, 114 and 120 which cooperate to define four vertical barriers 106, 112, 118, and 122 so as to define only one way travel through the ramp configuration 100. As indicated above, the cam member 68 is caused to move longitudinally away from the mounting block 84 by bending the prosthesis 20 which causes the displacement of the tension member 32, which in turn because of its fixed length, results in increased tension in the tension member 32. When the force of the tension member 32 exceeds that of the coil spring 70, the cam member 68 moves longitudinally away from the mounting block 84. Assuming the prosthesis 20 was in the flaccid state illustrated in FIGS. 1 and 3 such that the cam follower member 86 was in the positioned illustrated in FIGS. 1 and 3 at the time of bending the prosthesis 20, the cam follower end 86b would move as generally indicated by the arrow 92 from the surface 104 on the ramp configuration 100 to the surface 108. The cam follower end 86b is prevented from moving onto the surface 120 by the vertical barrier 122. The surface 108 allows for some over travel by the cam follower end 86b should the prosthesis be bent excessively. Upon cessation of the bending motion, the curvature of the prosthesis 20 will be reduced and the tension in the tension member 32 will be reduced. Accordingly, the coil spring 70 will bias the cam member 68 toward the mounting block 84 such that the cam follower end 86b will move from the surface 108 over the ramp 110 as generally indicated by the arrow 93 and onto the surface 114. The vertically extending barrier 106 will prevent the cam follower end 86b from moving back onto surface 104. The cam member 68 will continue to move toward the mounting block 84 under the influence of the coil spring 70 until the cam follower end 86b moves to the position generally indicated in FIGS. 2 and 4, whereupon its comes to rest proximate a vertical wall 130 of the cam member 68 where the force of the coil spring 70 is balanced by the force of the tension member 32. With the cam member 68 in the position shown in FIGS. 2 and 4, the prosthesis 20 is in a rigid or erect state since the tension member 32 is placed under tension by the coil spring 70 forcing the cam member toward the pivot block 84. In addition, the friction between the surfaces 56 and 54 of the radiused segments 50 is increased thereby providing the prosthesis 20 with substantial rigidity. If the prosthesis 20 is bent once again the increased tension in the tension member 32 will cause the cam member 68 to move longitudinally away from the mounting block 84. Assuming the cam follower member end 86b was in the position illustrated in FIGS. 2 and 4 at the time of bending the prosthesis 20, the cam follower end 86b will move as generally indicated by the arrow 94 from the surface 114 over the ramp 116 and onto the surface 120 since the cam follower end 86b is prevented from moving onto the ramp 110 by the vertical barrier 112. The surface 120 once again provides for some over travel by the cam follower end 86b should the prosthesis 20 be bent excessively. Upon cessation of the bending motion of the prosthesis 20, the curvature of the prosthesis 20 will be reduced and the tension in the tension member 32 will corresponding be reduced. Accordingly, the cam member 68 will be biased toward the mounting block 84 by the coil spring 70 such that the cam follower end 86b will move from the surface 120 onto the surface 104 since the barrier 118 will prevent the cam follower end 86b from moving back onto the ramp surface 116. The cam member 68 will continue to move longitudinally toward the mounting block 84 until the cam follower end 86b engages vertical wall 132 of the cam member 68 whereupon the cam member 68 is retained in position and further longitudinal movement toward the mounting block 84 is prevented. With the cam member 68 in the position illustrated in FIGS. 1 and 3, the prosthesis 20 is in a flexible or flaccid state since the tension member 32 is not under tension or reduced tension and the frictional forces between the adjacent surfaces 54 and 52 of the radiused segments 50 is decreased.

As previously indicated, the entire prosthesis 20 is preferably covered with the sheath 28 of physiologically inert and pliable material to shield the prosthesis from the body tissue so as to prevent tissue interference with its function and prevent tissue damage, the sheath 28 being wedgedly secured by the clamp members 38, 40 in cooperation with the members 46, 48 near the proximal and distal ends of the prosthesis 20. The applicants have found that expanded polytetrofloralethylene (PTFE), such as the product sold by Goretex Corporation under the trademark Goretex, coated with silicone rubber, is a suitable material. It will be appreciated that other elastomeric type, implantable materials might be utilized.

Most of the internal elements are preferably made of Titanium and stainless steel. However, the radiused segments 50 and possibly and the cam member 68 are preferably made of polysulfone. It will be appreciated that other suitable materials might be utilized.

Subsequent bending and unbending may be carried out for numerous repetitions with the prosthesis 20 being alternately rigid and flaccid. The prosthesis 20 thus exhibits bistable characteristics in that it maintains either of the states until being manually changed.

It has been found that an axial elongation of two to six millimeters wil generate adequate tension to maintain an erection.

In one embodiment of the present invention an axial tension member 32 is not utilized. The sheath 28 might be utilized as the primary tensioning member.

Illustrated in FIG. 9 is an enlarged cross-sectional view of one of the segments 50 and illustrated in FIGS. 10 through 15 is an alternate embodiment of the segments generally designated by the reference numeral 250. As with the segments 50, the segments 250 have a generally concave surface 252 proximate one end thereof and a convex surface 254 proximate the opposite end thereof. The segments 250 are oriented in an articulated column 226, as illustrated in FIG. 14, such that the adjacent surfaces of the segments 250 cooperate to form ball and socket joints 256. The articulated column 226, as with the previous embodiment, is journaled axially to receive a tension member 232. Moreover, as with the previous embodiment, the segments 250 are made from a surgically implantable material, preferably an implantable plastic such as polyurethane, polysulphone or polypropolene and are enclosed by a sheath 228 like that of the previous embodiment.

As previously discussed and as illustrated in FIGS. 1 through 4 and newly added FIG. 9, the previous embodiment of the segments 50 included the shoulder portion 51 about the periphery of the concave surface 52 and a corresponding shoulder portion 53 about the convex surface 54.

In the embodiment illustrated in FIGS. 10 through 15, a triangularly shaped protuberance 251 surrounds or circumvents the periphery of the concave surface 252 while a corresponding triangularly shaped indentation 253 surrounds or circumvents the periphery of the convex surface 254. As illustrated in FIGS. 14 and 15, facing ones of the protuberances 251 and indentations 253 on adjacent segments 250 are longitudinally aligned and longitudinally spaced apart when the articulated column 226 is relatively straight. when the articulated column 226 is bent, as illustrated in FIG. 15, the facing protuberances 251 and identations 253 will come together and interlock so as to prevent relative radial slipage between facing adjacent surfaces 252, 254 of the segments 250 and provide for controlled bending of adjacent ones of the segments 250 about a defined pivot point located in the base of the indentation. This enables a more uniform radius of curvature of the articulated column 226 when bent, since there is well-defined, predetermined pivot point between adjacent ones of the segments 250. Further, adjacent ones of the segments 250 will not slip relative to each other, thereby reducing the occurrence of irregulaties in the curvature of the articulated column 226. This increases the useful life of the prosthesis, since sharp edges are prevented from occurring along the bore of the articulated column 226 through which the tension member 232 extends which might otherwise cause additional wear on the tension member 232 and overall degraded performance of the cam actuated prosthesis. Additionally, slipage between adjacent ends of the segments 250 can create sharp edges proximate the periphery of the concave and convex surfaces 252, 254 which can interfere with the bending motion and cause irregularities in the radius of curvature. Futhermore, such slipage often creates undesirable noise caused by the surfaces rubbing against each other during the bending process. Additionally, since the protuberances 251 and the indentations 253 completely surround the concave 252 and the convex 254 surface areas, the interlocking function is provided regardless of the direction in which the articulated column 226 is bent. The interlock function is thus provided a full 360 degrees about the longitudinal axis of the articulated column 226.

In the embodiment shown in FIGS. 10 through 15, the protuberance 251 has two sides 261, 262. The sides 261, 262 form angles p₁ and p₂ each of substantially forty-five degrees relative to a plane 263 perpendicular with respect to a longitudinal axis of the articulated column 226. The embodiment of the indentation 253 has sides 271, 272 which form angles I₁ and I₂, respectively, of substantially forty-five degrees with respect to a line 273 which is off-set by an angle A of eight degrees from a line 274 perpendicular to the plane 263 and parallel to the longitudinal axis. In the embodiment shown, the indentation 253 is off-set so as to be directed slightly outward and away from the longitudinal axis of the articulated column 232 so as to enable the indentation 253 and the protuberance 251 to better line up when the segments 250 are bent, as generally illustrated in FIG. 15. It will be appreciated that other configurations and variations of indentations and protuberances might be utilized in keeping with the principles of the present invention.

Additionally, in the embodiment of the segments 250 shown in FIGS. 10 through 15, the convex surface 254 has a surface portion 280 which interconnects surface portions 281 and 282 at points substantially tangent to each of the surfaces 281, 282. The radius of curvature of the surface 280 is 0.050 inches, while the radius of curvature of the surfaces 281, 282 is 0.140 inches and 0.310 inches. This forms a larger opening 285 into a bore portion 289 of the segment 250 and reduces the sharpness of the surfaces which the tension member 232 might rub against by providing surfaces with uniform radii of curvature which are generally tangentially interconnected by a surface having a very slight radius of curvature. Both of these features will contribute to reduced wear on the tension member 232. The convex surface 252 is similarly formed of a surface 286 tangentially interconnecting surfaces 288, 287 wherein the surface 286 has a radius of curvature of 0.055 inches and surfaces 288, 287 have a radius of curvature of 0.310 inches and 0.140 inches, respectively. The likelihood that facing adjacent concave and convex surfaces 252, 254 of adjacent ones of the segments 250 will cause damage to each other during the bending process is reduced due to their similar configuration and the elimination of any rough edges.

Figure 16:
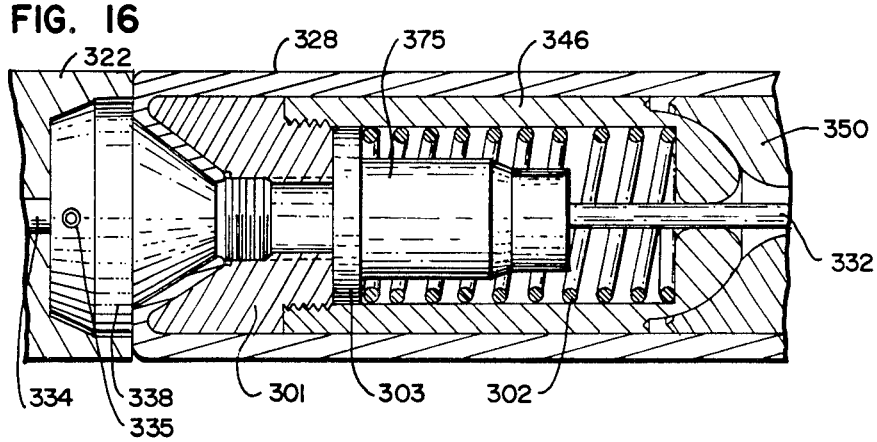
FIG. 16 is partial sectional view of an embodiment of a resilient biasing arrangement interconnected to one end of the tension member which is utilized on one embodiment of the present invention.
Figure 17:
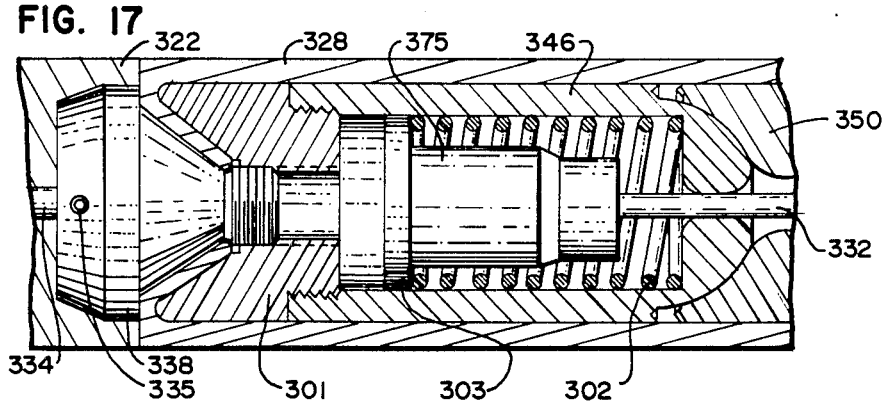
FIG. 17 is a view similar to FIG. 16 illustrating the end of the tension member interconnected to the resilient biasing arrangement when axially displaced due to a greater opposing force being placed on the tension member by excessive bending or distortion of the prosthesis.

Yet another embodiment of the present invention is illustrated in FIGS. 16 and 17. (FIGS. 16 and 17 illustrate only that portion of the prosthesis modified in this embodiment, the remaining portions not shown being similar to the previous embodiments.) In the previous embodiments, the tension member 32 was interconnected at one end to the anchor member 75 pivotally mounted inside of the terminator member 46. In the embodiment shown in FIGS. 16 and 17, the tension member 332 is suitably interconnected at one end to the anchor member 375 which is pivotally mounted inside of the terminator member 346. In the embodiment shown, the anchor member 375 is crimped onto the tension member 332. A coil spring 302 coaxially surrounds the anchor member 375 and is retained between an inner end of the terminator member 346 and a collar portion 303 of the anchor member 375. The coil spring 302 forces the anchor member 375 away from the inner end of the terminator member 346. A spring pre-load member 301 is threadedly secured at an opposite end of the terminator member 346 so as to force against the collar portion 303 and limit axial movement of the anchor member 375 such that the tension member 332 is not placed in tension by the coil spring 302 forcing against the collar portion 303. Accordingly, the coil spring 302 can be compressed varying amounts by threading the spring preload member 301 varying distances into the terminator member 346 so as to place the coil spring 302 under a predetermined load whereby the coil spring 302 exerts a predetermined axially directed force on the anchor member 375 and correspondingly, the tension member 332. The coil spring 302 will resist movement of the anchor member 375 as the tension member 332 is placed in tension when switching from the flaccid to the rigid state. Preferably, the axial biasing force exerted by the coil spring 302 is greater than the opposing axial force exerted on the tension member 332 when the prosthesis is switched to the rigid state by the actuator apparatus 30. Accordingly, during normal operation, that is, when switching from the flaccid to the rigid state, the anchor member 375 at the end of the tension member 332 will not be displaced. In certain embodiments, the coil spring 302 might exert an axially directed force of 10–12 pounds on the tension member 332, whereas the actuator apparatus 30 might cause a force of 7–8 pounds to be exerted on the tension member 332 when the prosthesis is switched to the rigid state and the tension member is placed in tension. However, should the prosthesis be subjected to extreme bending or distortion, the force exerted on the tension member 332 might exceed the force exerted by the coil spring 302 on the tension member such that the end of the tension member 332 interconnected to the anchor member 375 is displaced, an example of which is generally illustrated in FIG. 17. Accordingly, the resultant force exerted on the tension member 332 is reduced, thereby reducing the overall tension of the tension member 332. This minimizes the likelihood that the tension member 332 or other working parts of the prosthesis will be damaged due to the large forces to which subjected when the prosthesis undergoes extreme bending or distortion. Upon removal of the excessive force, the coil spring 302 will urge the end of the tension member 332 to which connected back into its normal position. It will be appreciated that other resilient biasing devices might be utilized in place of the coil spring 302 to exert an axially directed force on the anchor member 375. As illustrated, the pre-load member 301 is illustrated as being threaddedly interconnected to the clamp member 338 at the proximal end of the prosthesis, the clamp member 338 being interconnected to the proximal end portion 322 of the prosthesis by the pin member 334 and set screw 335 arrangement in a fashion similar to that of the previous embodiments. It will be appreciated that as with the actuator apparatus 30, the coil spring 302 biasing mechanism might be located proximate either end of the prosthesis or intermediate thereof. Moreover, the coil spring 302 might be located proximate the same end of the prosthesis as the actuator apparatus 30.

It is to be understood, however, even though numerous advantages and characteristics of the invention have been set forth in the foregoing description, together with details of the structure and function of the invention, the disclosure is illustrative only, and changes may be made in detail, especially in matters of shape, size and arrangement of parts within the principles of the present invention, to the full extent indicated by the broad general meaning of the terms in which the appended claims are expressed.

What is claimed is:

1. A penile prosthesis, comprising:
   (a) an elongated cylindrical body having a longitudinal axis and further having a distal end portion and a proximal end portion, said elongated cylindrical body including an outer elongated sheath formed from a physiologically inert and pliable material;
   (b) an articulated column of radiused segments disposed intermediate of said distal end portion and said proximal end portion, the radiused segments having a concave surface portion proximate one end and a convex surface portion proximate an opposite end, the facing concave and convex surfaces of adjacent ones of the radiused segments cooperating to form ball and sockets joints between adjacent ones of the radiused segments, a shoulder portion being positioned about a periphery of each of the concave and convex surfaces, the facing shoulder portions of adjacent ones of the segments cooperating to limit the amount of bending movement which occurs between adjacent ones of the segments;
   (c) an elongated tension member extending longitudinally of the elongated cylindrical body, the tension member being secured proximate first and second ends to proximate the distal end and proximal end portions of the prosthesis; and
   (d) switch means enclosed within the sheath for switching the prosthesis between a rigid state and a flexible state, the switch means cooperating with the tension member and the articulated column for increasing the tension in the tension member and compressing the articulated column when switching the prosthesis to the rigid state.

2. A penile prosthesis in accordance with claim 1, further including resilient biasing means interconnected to the tension member proximate one end of the tension member for exerting a predetermined axially directed force on the tension member such that if an opposing force is exerted on the tension member which is greater than the predetermined force, the end of the tension member will be displaced, thereby reducing tension and preventing damage to the tension member which might otherwise be caused by excessive bending or distortion of the prosthesis.

3. A penile prosthesis, comprising:
   (a) an elongated cylindrical body having a longitudinal axis and further having a distal end portion and a proximal end portion, the elongated cylindrical body including an outer elongated sheath formed from a physiologically inert and pliable material;
   (b) an articulated column of radiused segments disposed intermediate of said distal end portion and said proximal end portion, the radiused segments having a concave surface portion proximate one end thereof and a convex surface portion proximate an opposite end thereof, the facing concave and convex surface portions of facing ones of the radiused segments cooperating to form ball and socket joint means between adjacent ones of the segments for enabling slidable movement therebetween, the radiused segments having proximate the facing ends thereof cooperating identation and protuberance means for restricting radial movement between the facing ends of adjacent ones of the radiused segments, the indentation means being located proximate one end of the radiused segments and the protuberance means being located proximate the opposite end of the radiused segments;
   (c) an elongated tension member extending longitudinally of the elongated cylndrical body, the tension member being fixed against longitudinal movement at a first end, the articulated column being axially journaled about the tension member; and
   (d) switch means enclosed within the sheath for switching the prosthesis between a rigid state and a flexible state, the switch means cooperating with the tension member and the articulated column for increasing the tension in the tension member and compressing the articulated column when switching the prosthesis to the rigid state.

4. A penile prosthesis in accordance with claim 3, further including resilient biasing means interconnected to one end of the tension member for exerting a predetermined axially directed force on the tension member whereby upon application of a greater opposing force on the tension member, the end of the tension member is displaced, thereby reducing tension in the tension member and reducing the likelihood that the tension member will be damaged due to excessive bending or distortion of the prosthesis.

5. A penile prosthesis in accordance with claim 3, wherein the indentation means and the protuberance means circumvent the concave and convex surface portions of the radiused segments.

6. A penile prosthesis in accordance with claim 3, wherein the concave and convex surface portions include three surface areas having different radii of curvature from one another, two of the surface areas being tangentially interconnected to an intermediate one of the surface areas.

7. A penile prosthesis comprising:
   (a) a distal end;
   (b) a proximal end;

(c) an outer elongated sheath formed from physiologically inert and pliable material;

(d) an articulated column of segments disposed intermediate of the distal end and the proximal end, the segments having a concave surface portion proximate one end and a convex surface portion proximate an opposite end, the facing concave and convex surface portions of facing ones of the segments cooperating to form ball and socket joint means between adjacent ones of the segments for enabling slidable movement therebetween, interlocking means including cooperating protuberance and identation means being positioned proximate the facing ends of the segments and surrounding the concave and convex surface portions of the segments for restricting radial slippage between the facing ends of adjacent ones of the segments whereby the likelihood that the segments will become disjointed is reduced;

(e) an actuator apparatus disposed intermediate of the articulated column and one of the distal and proximal ends, the actuator apparatus including a cam member and a cam follower member;

(f) biasing means cooperating with the actuator apparatus to longitudinally bias the cam member and the cam follower member toward one another; and (g) tension means cooperating with the actuator apparatus to longitudinally bias the cam member and the cam follower member away from one another when the tension means is placed in tension, the tension means causing the cam member and the cam follower member to longitudinally move apart when placed in sufficient tension to overcome the biasing means, the tension means being place in sufficient tension by applying a bending force on the prosthesis to cause bending of the same, the cam member and the cam follower member moving longitudinally toward one another upon removal of the bending force, the cam member and the cam follower member alternately coming to rest at a first and second relative longitudinal displacement between one another upon removal of the bending force, the cam member and the cam follower member being farther apart in the first relative longitudinal displacement, the actuator apparatus cooperating with the tension means to compress the articulated column when in the second relative longitudinal displacement and further cooperating with the tension means to place the articulated column in an non-compressed state when in the first relative longitudinal displacemnt.

8. A penile prosthesis in accordance with claim 7, wherein the concave and convex surface portions include three surface areas having different radii of curvature from one another, the three surface areas including outer surface areas interconnected to an intermediate surface areas so as to provide a continuous surface area.

9. A penile prosthesis in accordance with claim 8, wherein the intermediate surface area has a radius of curvature less than the other two surface areas.

10. A penile prosthesis in accordance with claim 7, wherein the indentation means circumvents the convex surface portion and the protuberance means circumvents the concave surface portion.

11. A penile prosthesis in accordance with claim 7, wherein the indentation means and protuberance means have a cooperating triangular configuration in cross-section.

12. A penile prosthesis in accordance with claim 11, wherein the indentation means is canted outwardly with respect to a longitudinal axis of the articulated column thereby providing for better alignment between the protuberance means and the identation means when the articulated column is bent.

13. A penile prosthesis in accordance with claim 7, further including resilient biasing means interconnected to the tension means proximate one end of the tension means for exerting a predetermined axially directed force on the tension means such that if an opposing force is exerted on the tension means which is greater than the predetermined force of the resilient biasing means, the end of the tension means is displaced thereby preventing damage to the tension means which might otherwise be caused by excessive bending or distortion of the prosthesis.

* * * * *

UNITED STATES PATENT AND TRADEMARK OFFICE
CERTIFICATE OF CORRECTION

PATENT NO. : 4,619,251
DATED : October 28, 1986
INVENTOR(S) : Richard A. Helms, et al.

It is certified that error appears in the above-identified patent and that said Letters Patent is hereby corrected as shown below:

In the title, line 2, before "MEMBER" insert --TENSION--.

Col. 1, line 46, delete "prosthesis" and insert --prostheses--.

Col. 1, line 68, delete "facings" and insert --facing--.

Col. 2, line 59, delete "flacid" and insert --flaccid--.

Col. 5, line 7, after "is" insert --a--.

Col. 5, lines 58-59, delete "flexible/-flaccid" and insert --flexible/flaccid--.

Col. 6, line 32, delete "mechaniam" and insert --mechanism--.

Col. 6, line 36, delete "securedly" and insert --securely--.

Col. 8, line 2, delete "securedly" and insert --securely--.

Col. 9, line 6, delete "positioned" and insert --position--.

Col. 9, line 53, delete "corresponding" and insert -correspondingly--.

Col. 10, line 19, delete "and" (second occurrence).

Col. 10, line 28, delete "wil" and insert --will--.

Col. 10, line 66, delete "when" and insert --When--.

Col. 11, line 2, delete "slipage" and insert --slippage--.

Col. 11, line 7, after "is" insert --a--.

Col. 11, line 11, delete "irregulaties" and insert --irregularities--.

Col. 11, line 18, delete "slipage" and insert --slippage--.

Col. 11, line 23, delete "slipage" and insert --slippage--.

UNITED STATES PATENT AND TRADEMARK OFFICE
CERTIFICATE OF CORRECTION

PATENT NO. : 4,619,251

DATED : October 28, 1986

INVENTOR(S) : Richard A. Helms, et al.

It is certified that error appears in the above-identified patent and that said Letters Patent is hereby corrected as shown below:

Col. 14, line 34, delete "cylndrical" and insert --cylindrical--.

Col. 15, line 34, delete "place" and insert --placed--.

Col. 16, line 14, delete "areas" and insert --area--.

Signed and Sealed this

Seventh Day of April, 1987

Attest:

DONALD J. QUIGG

Attesting Officer

Commissioner of Patents and Trademarks